United States Patent
Tobiason

(10) Patent No.: US 10,085,443 B2
(45) Date of Patent: Oct. 2, 2018

(54) METHOD AND FORMULATION FOR REMOVING FLORA FROM SEWER LINES

(71) Applicant: OLVIDIUM, INC., Columbus, NE (US)

(72) Inventor: Timothy Wayne Tobiason, Columbus, NE (US)

(73) Assignee: Olvidium, Inc., Columbus, NE (US)

( * ) Notice: Subject to any disclaimer, the term of this patent is extended or adjusted under 35 U.S.C. 154(b) by 111 days.

(21) Appl. No.: 14/189,531

(22) Filed: Feb. 25, 2014

(65) Prior Publication Data
US 2014/0179533 A1    Jun. 26, 2014

Related U.S. Application Data

(63) Continuation of application No. 13/317,503, filed on Oct. 20, 2011, now abandoned.

(51) Int. Cl.
*A01N 25/30*   (2006.01)
*A01N 37/34*   (2006.01)

(52) U.S. Cl.
CPC ............ *A01N 25/30* (2013.01); *A01N 37/34* (2013.01)

(58) Field of Classification Search
CPC ......... A01N 25/30; A01N 37/34; A01N 25/16
USPC ........................................ 504/310
See application file for complete search history.

(56) References Cited

U.S. PATENT DOCUMENTS

| | | |
|---|---|---|
| 2,397,328 A | 3/1946 | Ripley |
| 2,763,288 A | 9/1956 | Tharp |
| 3,197,302 A | 7/1965 | Macbride |
| 3,635,230 A | 1/1972 | Kirschke |
| 3,655,122 A | 4/1972 | Brown et al. |
| 3,892,588 A | 7/1975 | Home |
| 4,425,154 A | 1/1984 | Meyer |
| 4,556,434 A | 12/1985 | Woogerd |
| 4,781,329 A | 11/1988 | Tenney |
| 4,944,320 A | 7/1990 | Waite et al. |
| 5,020,188 A | 6/1991 | Walton |
| 5,062,878 A | 11/1991 | Tobiason |
| 5,069,706 A * | 12/1991 | Tobiason ............... A01N 25/16 504/183 |
| 5,081,545 A | 1/1992 | Wells |
| 5,165,434 A | 11/1992 | Tobiason |
| 5,544,447 A | 8/1996 | Easey et al. |
| 5,658,851 A * | 8/1997 | Murphy ............... A01N 25/30 424/405 |
| 5,919,731 A | 7/1999 | Malavenda |
| 6,841,518 B2 * | 1/2005 | Malavenda ............ A01N 43/40 504/250 |
| 2006/0180677 A1 | 8/2006 | McManic et al. |

OTHER PUBLICATIONS

TACTIC™ Product Label and Application Information (Loveland Products Inc. published on Jan. 2009).*
Timothy W. Tobiason, A Short History of Toby's Foaming Root Killer Aug. 13, 2011 3 Pages USA.
Catherine Wo PHD, Physical & Chemical Characteristics of Oblitiroot Sep. 19, 2011 16 Pages USA.
Carolyn Lowe LATG, Dermal Synsitization Study in Guinea Pigs Oct. 13, 2011 25 Pages USA.
Carolyn Lowe LATG Primary Skin Irritation Study in Rabbits Oct. 13, 2011 16 Pages USA.
Carolyn Lowe LATG Acute Inhalation Toxicity Study in Rats Oct. 13, 2011 25 Pages USA.
Carolyn Lowe LATG Acute Oral Toxicity Up & Down Procedure in Rats Oct. 13, 2011 16 Pages USA.
Carolyn Lowe LATG Acute Dermal Toxicity Study in Rats Oct. 13, 2011 16 Pages USA.

* cited by examiner

*Primary Examiner* — Mina Haghighatian
*Assistant Examiner* — Mei Ping Chui

(57) ABSTRACT

This invention relates to the application of herbicides in sewer liens to kill tree roots inside the lines and preventing re-growth into the lines for years after application. It relates to the discovery that latex polymers, organosilicone surfactants, deposition agents and other surfactants can be used to "glue" the herbicides to pipe surfaces. This discovery allows the use of plant killing herbicides to treat roots in sewer lines—killing them—which results in their subsequent removal by decay and erosion processes. It also allows for the use of the herbicides to prevent regrowth back into the sewer lines by applying the herbicides in a compound which adheres to the sewer line surfaces and forms a long term coating on the pipe and joint surfaces where the roots might attempt to grow back in. The compound resists erosion and washing away preventing long term root re-infestations in the sewer lines.

14 Claims, No Drawings

METHOD AND FORMULATION FOR REMOVING FLORA FROM SEWER LINES

This application is a continuation to co-pending U.S. patent application Ser. No. 13/317,503 filed Oct. 20, 2011, the entire disclosures of which are incorporated herein by reference.

BACKGROUND

Trees absorb water and other compounds present in the water such as herbicides and trace minerals. The Xylem then transports water throughout the tree by use of the water gradient. Water moves from areas of excess water (roots) to areas of less water (trunk and branches) via the xylem. Roots normally absorb and retain large amounts of water and this water moves from the roots to the stem and then to the leaves. This method of transport does not require living cells or living processes and occurs independently. The phloem generally moves sap from the leaves to the roots and requires living cells and processes to mediate this transport. Living cells are also required for cell to cell transport.

Many methods have been used in the past to kill tree roots and remove them from a sewer line using chemical rather than mechanical methods. These have included—

1. The use of hot water which uses heat to kill the roots. This requires the heating of water to near boiling point and then soaking the line with it. The disadvantages are the great cost of heating the water and the problems of taking a sewer line out of service during the treatment period.
2. The application of inorganic salts, most notably Copper Sulfate. Although copper sulfate is still used in some households, its use has been banned in many states due to toxicity problems with copper in treatment plants (it kills the necessary treatment bacteria) and discharge into rivers and streams resulting in toxic loads which kill fish and other aquatic organisms. Other inorganic salts and corrosive acids and bases which are less toxic to the environment are not supported for registration with EPA and may not therefore be used in this type of application.
3. Dichlobenil has been used successfully for many years in sewer line root control. Support for its registration has been suspended in some areas by its manufacturer (due to testing expenses). It kills roots on contact in low doses and prevents root re-growth for several months as long as it is not washed away. It does not kill the roots more than 1-2" back from the contact site which limits its effect.
4. Metham Sodium has been used for decades in sewer line root control and as a fungicide fumigant. It yields a poisonous and caustic gas which kills roots very effectively (100%) inside the pipe and outside the pipe where the gas travels. Its disadvantages are its effects on humans (it causes burns similar to that of mustard gas) and its effect on non-target vegetation and surrounding environment. It kills treatment plant bacteria, fish and other aquatic organisms in tiny doses. The environmental effects are usually small but have been disastrous in highly publicized circumstances such as tanker car leaks.
5. Diquat came into sewer line use in 1999. It is very environmentally friendly and generally kills roots on contact. It has had mixed results in the industry, being rejected after testing by large municipalities for inconsistent results. This is due to the fact that Diquat is rapidly inactivated by organic materials in soils and detritus on roots. Roots are often coated with debris which consists largely of fatty acids, waste products, tissue paper, etc. which absorbs the Diquat and binds it in a form which makes it inactive. This results in treatments in which clean roots are killed and coated roots are generally unaffected. Since roots filter the flow of water through them in the sewer lines, they very often have a significant buildup of organic detritus which prevents the Diquat from reaching it intact. This results in spotty and inconsistent root kill.
6. It is also known that salts of sulfamic acid such as ammonium, magnesium, potassium and sodium sulfamate also have root killing properties. The ammonium salt form is systemic and can kill the entire tree in sufficient amounts and because of this has not been used commercially in this application. The use of the sodium sulfamate salt in the commercial application of "Root-X with Dichlobenil" has been used with modest success since 1990.

Some of the above chemicals may be delivered into the sewer lines and onto the tree roots to be effective. Some methods include—

A. Delivering the herbicide with the flow of water and hoping that the chemical is captured and/or absorbed onto the roots in necessary quantities to kill them. Some of the chemicals are produced in the form of a solid cube (copper sulfate) which ideally becomes entangled in roots partially retarding the flow in the bottom of the sewer line. These roots absorb the copper and die.
B. Spraying on the pipe surfaces and roots with a water carrier. The herbicide is washed away with the water flow leaving almost no amount to be absorbed onto the roots. Some of the water herbicide mix is expected to displace water present in the root mass and detritus and thereby effect some root kill. Soaking of the sewer lines for at least an hour has yielded good results commercially with this method.
C. The use of foam which slows and further reduces the drainage of water and herbicide. This has been accomplished by using air compressors to generate the gas and surfactants to generate the foam. Foam has also been achieved using chemicals which release reaction compounds when brought together in water ($CO_2$ from sodium bicarbonate and acid) with surfactants. When the foam is chemical and used as gravity flow delivery it travels down the pipe until it collides with roots hanging down and becomes obstructed or diminished and does not get on further root intrusions at joints downstream unless that are hanging down in the water flow. This has been a significant disadvantage when using a single pour in application method.
D. The application into the line as a gas (Metham Sodium gas, Dichlobenil known as Vapo Rooter). This method is effective but is environmentally undesirable and hazardous to humans who come into contact with it.
E. The application into the line as a dry dust blown in using air pressure. This method, while effective would blow the dust out of vents above houses and into homes with dry traps creating undesirable effects and has not been adopted commercially.

These various techniques have an array of drawbacks. Accordingly, there is a need for a foaming root killer composition drastically reduce the environmental load of herbicide, prevents root re-growth in sewer lines long term and saves homeowners and municipalities money on repeat applications and pipe replacement.

SUMMARY

This disclosure encompasses drastically improved methods of foam delivery in which a foam is generated by reaction of sodium bicarbonate, a dry acid such as sulfamic acid, a surfactant mix and polymer binders such as synthetic latex and betaine group surfactants. The reaction yields a by-product of CO2 gas making the foaming agent environmentally inconsequential. The use of polymer binders allows the formation of a long lasting coating which sticks to the pipe surfaces and is not washed down the sewer line with the water flow like other foaming applications in the past.

In general, the bulk of the applied active ingredient remains in the sewer line long term (unless or until it is eroded away in small amounts). This reduces the potential herbicide load at any given time which reaches the treatment plant to undetectable levels for all practical purposes. By using polymers which are highly resistant to erosion (synthetic latex) this effect is further enhanced.

An additional aspect of this disclosure is an improved spreading and absorption of the mix onto the root surfaces and into the root cells by the use of soybean oil, silicone polyether copolymer and surfactants.

In this particular instance, the drastic improvement comes from the use of surfactants which are sticky and which are mixed with synthetic latex and organosilicone polymers, and soybean oil to produce a sticky foam which leaves a coating on (adheres to) solid surfaces and roots. The thick pasty foam slowly collapses into the sticky coating similar to a mix of hand cream and glue which solidifies onto the surfaces and roots and persists for weeks, months and years resisting erosion and decay. This insures long term contact and prevention of root re-growth in the vicinity of the herbicide saturated coating. Current industry practices create a foam mix which is designed to fill the entire pipe volume with a herbicide foam mix which then drains away entirely which is wasteful, inefficient and delivers the entire applied herbicide load directly to the treatment plants downstream.

This method does not require filling the entire pipe. The herbicides can now be applied as a foam (or spray) coating to the interior pipe surfaces and roots by spray, sponge, brush, sticky foam mass, compressed air fog and so on. This use of a single formula which lends itself to so many types of application methods is in itself of great benefit to the industry. It allows municipalities to use whatever equipment is on hand that they have used previously in sewer line cleaning and root control applications. It also has the obvious benefit of using much smaller amounts of herbicide materials to kill and remove the roots from the sewer lines since the entire pipe volume does not need to be filled with herbicide saturated foam any longer.

DETAILED DESCRIPTION

Based on previous commercial experience in the trade and preliminary testing, a decision was made to continue use of Dichlobenil(2,6 dichlorobenzonitrile) as the main active ingredient in the present formulations. Work began on new ways of creating a way of coating the sewer pipe, roots and joints, with a paint or glue-like coating which would resist water erosion and stay in the line long term, ideally for many years preventing root re-growth, pipe damage from root diameter growth, and pipe obstructions.

The use of synthetic latex and organosilicone mixtures used in the crop-dusting industry was found to be advantageous. These substances known in the trade as BOND and TACTIC are manufactured by Loveland Products in Loveland Colo. These formulas enhance droplet deposition and rain fastness (weatherproofing) reducing pesticide run-off and increase effectiveness of fungicidal and insecticidal sprays. They also improve spreading ability of the mixture coating the entire surface of the target plant tissues, joints, and pipes.

A variety of surfactants were examined for inclusion in the formulations. Triethanolamine laurel sulfate surfactant (ULTRAFAX TLS) which was found to produce enhanced foam volumes. In some formulas, betaine group surfactants (ULTRAFAX B352-both surfactants are manufactured by MFG Chemical Co of Dalton Ga.) were added to great effect. These were found to be far more effective than many other surfactants/surfactant groups tested. These surfactants yielded a foam that resisted collapse for 30 minutes or more and by themselves would leave a water resistant film on target surfaces.

The final critical ingredient we added is an oil. In particular, soybean oil was found to be effective. Surprisingly, raw soybean oil was found to be more effective than methylated soybean oil in creating the desired foam, stickiness, and also improved penetration into the root cells.

The present formulas were compared with a previous foaming root killer (sold as ROOT-X in the trade)

US PATENTS

U.S. Pat. No. 5,062,878 1991 Tobiason
U.S. Pat. No. 5,069,706 1991 Tobiason
U.S. Pat. No. 5,165,434 1992 Tobiason
U.S. Pat. No. 5,361,512 1994 Tobiason Testing on potted plant roots indicated significant improvement over the previous patented formulas. When the 2 parts of the root killer are brought together without added water, a thick, paste-like foam is produced. By weighing the applications of the old and new treatments it was discovered that as much as 100 times as much root killer by weight could be deposited onto the roots after run-off a few minutes later.

The present formulations also strongly resisted wash off leaving a uniform film coating the roots and pipe surfaces. When pressed or sprayed into joint openings, the root killer accumulated in large amounts leaving behind a thick barrier which would remain and prevent future root intrusion through the openings. All previous root killer applications in sewer lines easily wash away and leave no long term prevention of detectable volume in the pipe and joints. The present method and formulations solve this and other shortcomings.

The use of polymers that would be more resistant to water flow erosion and decay was also investigated. The herbicide industry has long used polymers as "stickers" to apply herbicides to plant leaves in aerial spraying to minimize runoff and drift. Some polymers tested were found to be good at adhering to roots. The result was to create a long lasting coating that would be strongly resistant to water flow erosion and decay processes so that long term root regrowth may be prevented months to years later.

It is known and previously published in various textbooks and patents that herbicides translocate via the xylem which moves water and uses the water gradient for direction of flow. Herbicides also translocate via the phloem which moves sap from leaves to other plant parts and also by cell to cell via various cellular processes.

The commercial adjuvants BOND and TACTIC improve the deposition of the active ingredient Dichlobenil and foaming salts formed by the reaction of the 2 parts (in the case of the present formulation sodium sulfamate). These improvements include drastically increased retention of the foam on the root and pipe surfaces, resistance to run off, spreading and coating of all surfaces at the microscopic level, and thereby improving penetration into the root tissues and detritus surrounding the roots. Soybean oil is also well known in the crop-dusting trade to assist translocation and uptake into the plant tissues of substances contained in it.

The mixture was prepared in various ratios and tested on potted plant roots. Part of the pot container was cut out at the base so that the roots could be seen. The exposed roots were dosed with the foam mixtures and observed. The plants were also watered and the foam was dipped in water to see how much would wash off.

The plants used were hibiscus species and the effects of the foaming root killer were readily identified by the blackening of the roots along the length inward beginning at the meristems. Dead roots were identified visually by the loss of root hairs within 72 hours (and subsequent decomposition) on treated roots vs. untreated roots. Root kill was typically 1-2 inches from the applied foam. After 2 weeks no new root growth was observed in the treated areas and significant foam residue was clearly visible.

When the 2 parts of the formula are brought together, a small amount of foaming ensues yielding a thick sticky paste that does not run off or down target surfaces. When water is added to the mix, the mass is diluted and some of the mix will run down roots and pipes to the bottom. The greater the water dilution, the runnier the mix becomes, however, even large dilutions with significant run off still leaves behind a thin sticky film which bonds to the roots and pipes.

The dichlobenil and sulfamate salts from the foam mixture are believed to be absorbed into the root tissues thereby killing them. After death, regrowth of roots into the line later is inhibited by the action of the dichlobenil on the meristems (it has the effect of stopping cell division at meristem tips even when present in miniscule amounts).

The environmental benefits of this new formulation are that much of the root killer applied remains in the sewer pipe long term reducing the load on the waste stream and sewer plant. Less root killer is required to treat a line and long term effects reduce or eliminate the need for frequent re-treatments. Effective prevention of pipe damage from root growth obviates the necessity of digging up and replacing the lines which is very expensive and in some cases of large municipal main lines, practically impossible.

Concurrent with the new herbicide testing, the new foaming formula was developed as an improved delivery vehicle for the herbicides. The consistency of the formula allows it to be poured into the toilet bowl and flushed into the pipe. It can also be poured into manholes and washed down larger municipal lines. When it is mixed together it can be sent down the line through a cleanout or with municipal water flow. The thick mass can be brushed on or rolled on by using attachments on rooter cables which push, roll or brush the foam mass onto the pipe surfaces, roots and joints. This eliminates the need to fill the entire pipe volume with foam and also allows the root killer to be applied in an undiluted coating on the surfaces and joints. Little is left to run off into the waste-stream flow. The liquid part B can also be sprayed in directly onto the roots and pipe surfaces using equipment on hand in the rooter industry. In addition, it can be applied using brushes and rollers used in the paint industry and adapted to use on the end of rooter cutting cables to push or brush the foam onto and into the roots, pipe surface and joints.

Long term performance in the pipe is anticipated to be satisfactory. The paste could erode away over time with persistent water flow and would also decay away do to biological processes in the pipe. The use of synthetic latex in the formula retards these processes while still allowing the herbicide to do its work.

By using a mix of Synthetic Latex and organosilicone surfactant it was possible to produce a very sticky material that could be delivered as a self-foaming coating, a spray on coating, a brush on coating and even fogged into a sewer line as an aerosol. Additives were included to improve the material handling and coating properties and included soybean oil (which acts in a manner similar to wood stains and aids in penetrating root tissues), The new herbicide concept lends itself to application as a liquid spray, a self-foaming coating mass, an aerosol, a brush on coating and an air compressor based foam.

It is also clear that these benefits of the presently disclosed methods and formulations may have applications well beyond those found in sewer line applications.

Some embodiments embodiment may utilize one or more active ingredients, inorganic gas releasing compounds, one or more surfactants, one or more commercial adjuvants and an oil. Of particular interest as a result of testing was the following formulation:
Part A Sulfamic acid 22% gas releasing and sulfamate salt
Part B Sodium bicarbonate 25% gas releasing and sulfamate salt
   Soybean Oil 31% Deposition, penetrant, translocation aid
   ULTRAFAX B352 10% Foaming surfactant
   ULTRAFAX TLS 7% Foaming surfactant
   TACTIC 1% Sticker and deposition aid
   BOND 1% Spreader, sticker deposition aid
   Dichlobenil 50% 3% Active ingredient root killer
   Part A was a sulfamic acid by itself as a dry solid.

Part B was mixed together in the order shown above until it thickened to a consistency like maple syrup or motor oil. This part can be directly sprayed onto pipe surfaces and roots and will adhere to them with little drainage. The thick viscous liquid can be sprayed onto pipe surfaces with sewer washing and spraying equipment currently in use in the industry. It can also be foamed in using air compressor technology described in the cited patent references.

This formula can also be self-foamed into a sewer line by simply adding the 2 parts together in a toilet bowl and flushing. The formula for toilet bowl treatments is approximately 4# of both parts.

The above amounts can be adjusted to fit foaming a 4" line, 6" line or 8" municipal main line. The dose would remain the same for the pipe length to be treated but additional foaming compound ingredients are added to increase as the volume of pipe increases which is necessary to cover the increased surface areas.

Self foaming is often used to avoid using application equipment but heavy root masses often limit its reach in 300' city main lines by blocking most of the flow of the foam.

After application of the foaming root killer, any visible coating on the roots effects 100% root kill.

The amounts (by weight) of active ingredient used in the above applications are smaller than those used previously in the industry. That makes the present formulations and methods of great benefit from an environmental and cost standpoint.

It will be obvious to anyone skilled in the art, after having been made aware of the disclosure herein, that other chemical or mechanical device capable of generating gas will work in applying our new root killer formula and may also be used in practicing the methods and formulations disclosed.

Further, any compound capable of producing a phytocidal effect in flora roots or deterring the growth of flora roots, may be utilized as a herbicide in the practice of the claimed invention.

What is claimed is:

1. An herbicide formulation for application to plant root parts and/or sewer pipe surfaces comprising:
a herbicide in an amount of 3% by weight of the herbicide formulation;
an acid in an amount of 22% by weight of the herbicide formulation;
a carbonate or bicarbonate salt in an amount of 25% by weight of the herbicide formulation;
a polymer binder;
an organosilicone adjuvant, wherein the polymer binder and the organosilicone adjuvant are present in a combined amount of 2% by weight of the herbicide formulation;
a seed crop oil in an amount of 31% by weight of the herbicide formulation; and
a surfactant in an amount of 17% by weight of the herbicide formulation;
wherein the herbicide formulation produces a foam upon mixing.

2. The herbicide formulation of claim 1 wherein the herbicide comprises 2,6-dichlorobenzonitrile.

3. The herbicide formulation of claim 1 wherein the acid comprises sulfamic acid.

4. The herbicide formulation of claim 1 wherein the carbonate or bicarbonate comprises sodium bicarbonate.

5. The herbicide formulation of claim 1 wherein the polymer-binder comprises a synthetic latex.

6. The herbicide formulation of claim 1 wherein the organosilicone adjuvant comprises a silicone polyether copolymer.

7. The herbicide formulation of claim 1 in which the seed crop oil comprises soybean oil.

8. The herbicide formulation of claim 1 in which the surfactant comprises a surface active agent selected from the group consisting of triethanolamine laurel sulfate, a compound having a betaine group, and mixtures thereof.

9. The herbicide formulation of claim 8 in which the surfactant comprises at least one of triethanolamine laurel sulfate and cocamidopropyl betaine.

10. The herbicide formulation of claim 1, wherein:
the herbicide comprises 2,6-dichlorobenzonitrile;
the polymer-binder comprises a synthetic latex;
the organosilicone adjuvant comprises a silicone polyether copolymer; and
the surfactant comprises a surface active agent selected from the group consisting of triethanolamine laurel sulfate, a compound having a betaine group, and mixtures thereof.

11. A method of delivering the herbicide formulation of claim 1 to a plant root part in sewer line and/or a sewer pipe surface comprising:
providing an effective amount of the herbicide formulation; and
applying the effective amount of the herbicide formulation to the plant root part in sewer line and/or the sewer pipe surface, the step of applying comprising at least one of spraying, foaming, brushing, or rolling.

12. A method of inhibiting growth of plant root parts in sewer lines comprising:
providing a first mixture, the first mixture including:
a herbicide;
a carbonate or bicarbonate salt;
a polymer binder;
an organosilicone adjuvant; and
a seed crop oil; and
providing a second mixture, the second mixture including:
an acid; and
an aqueous surfactant admixture; and
mixing the first mixture with the second mixture to provide an herbicide mixture for application to at least one of a plant root part or a sewer pipe surface, the herbicide mixture comprising:
the herbicide in an amount of 3% by weight of the herbicide mixture;
the carbonate or bicarbonate salt in an amount of 25% by weight of the herbicide mixture;
the polymer binder;
the organosilicone adjuvant, wherein the polymer binder and the orqanosilicone adjuvant are present in a combined amount of 2% by weight of the herbicide mixture;
the seed crop oil in an amount of 31% by weight of the herbicide mixture;
the acid in an amount of 22% by weight of the herbicide mixture; and
the aqueous surfactant admixture in an amount of 17% by weight of the herbicide mixture.

13. The method of claim 12 in which the herbicide comprises 2,6-dichlorobenzonitrile.

14. The method of claim 12 wherein the polymer-binder is synthetic latex.

* * * * *